United States Patent [19]

Hsu

[11] Patent Number: 5,292,762

[45] Date of Patent: Mar. 8, 1994

[54] HALOPROPARGYL COMPOUNDS, COMPOSITIONS, USES AND PROCESSES OF PREPARATION

[75] Inventor: Adam C. Hsu, Lansdale, Pa.

[73] Assignee: Rohm and Haas Company, Philadelphia, Pa.

[21] Appl. No.: 530,770

[22] Filed: May 29, 1990

Related U.S. Application Data

[63] Continuation-in-part of Ser. No. 370,373, Jun. 22, 1988.

[51] Int. Cl.$^5$ ............... C07D 285/13; C07D 285/135; A01N 43/82
[52] U.S. Cl. .................................... 514/363; 514/340; 546/277; 548/136; 548/138
[58] Field of Search ............... 548/136, 138; 514/363, 514/340; 546/277

[56] References Cited

U.S. PATENT DOCUMENTS

| | | | |
|---|---|---|---|
| 4,639,460 | 1/1987 | Rose | 514/369 |
| 4,647,572 | 3/1987 | Inouye | 514/381 |
| 4,764,527 | 8/1988 | Wagner | 514/407 |

Primary Examiner—Robert Gerstl
Attorney, Agent, or Firm—Michael B. Fein

[57] ABSTRACT

Compounds of the formula

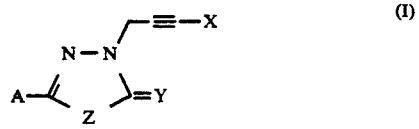

wherein
A is selected from the group consisting of hydrogen, alkyl, aryl, and heterocyclic;
Y and Z are independently selected from the group consisting of O, S, and N—R;
R is selected from the group consisting of hydrogen, substituted or unsubstituted alkyl, substituted or unsubstituted alkenyl, substituted or unsubstituted alkynyl, substituted or unsubstituted phenyl, and substituted or unsubstituted heterocyclic; and
X is selected from the group consisting of I and Br.

are disclosed to useful as antimicrobials.

6 Claims, No Drawings

HALOPROPARGYL COMPOUNDS, COMPOSITIONS, USES AND PROCESSES OF PREPARATION

This application is a continuation-in-part of Ser. No. 370,373 of Jun. 22, 1988.

BACKGROUND OF THE INVENTION

1. Field of the Invention

This invention relates to control of microorganisms.

2. Description of the Prior Art

Certain classes of iodopropargyl compounds have been proposed as fungicides or microbicides but no compound within those classes has achieved commercial success.

U.S. Pat. No. 4,616,004 to Edwards discloses fungicidal activity for compounds of the formula U.S. Pat. No. 4,639,460 to Rose shows compounds of the formula as fungicides.

U.S. Pat. No. 4,520,023 to Schmitt shows 3-(3-iodopropargyl)benzo-1,2,3-triazolin-4-ones and their use as microbicidal agents.

There was no suggestion in the prior art that compounds within the formula of the present invention would have utility in controlling microorganisms.

SUMMARY OF THE INVENTION

It is an object of the present invention to provide new compounds for controlling microorganisms.

A further object is to provide methods of making such compounds, methods of using them, compositions comprising such compounds, and uses of such compositions.

These objects, and others which will become apparent from the following disclosure, are achieved by the present invention which comprises in one aspect compounds of the formula (I)

wherein

A is selected from the group consisting of hydrogen, alkyl, aryl, and heterocyclic;

Y and Z are independently selected from the group consisting of O, S, and N—R,

R is selected from the group consisting of hydrogen, substituted or unsubstituted alkyl, substituted or unsubstituted alkenyl, substituted or unsubstituted alkynyl, substituted or unsubstituted phenyl, and substituted or unsubstituted heterocyclic; and X is selected from the group consisting of I and Br.

In another aspect the invention comprises a method of preparing such compound comprising reacting compound of the formula (V)

with an iodinating or brominating agent.

A further aspect comprises using a composition comprising the compounds, or the compound itself, to protect a material selected from the group consisting of wood, paint, adhesive, glue, paper, textile, leather, plastics, cardboard, lubricants, cosmetics, food, caulking, feed and industrial cooling water from microorganisms.

DETAILED DESCRIPTION OF THE INVENTION AND THE PREFERRED EMBODIMENT

The compounds of the invention are of formula I as set forth above. The more preferred embodiments are those wherein A is selected from the group consisting of hydrogen; ($C_1$ to $C_{18}$) straight or branched alkyl; ($C_3$ to $C_8$) cycloalkyl; ($C_3$ to $C_6$) alkenyl; ($C_3$ to $C_5$) alkynyl; ($C_7$ to $C_{12}$) aralkyl; ($C_6$ to $C_{12}$) aryl; ($C_6$ to $C_{12}$) aryl substituted with 1 to 3 substituents selected from the group consisting of halogen, ($C_1$ to $C_4$) alkyl, ($C_1$ to $C_4$) alkoxy, nitro, cyano, carboxyl ($C_1$ to $C_4$) alkoxycarbonyl, ($C_1$ to $C_4$) alkyl thio, -S(O)n$R^2$ where n is 1 or 2 and $R^2$ is ($C_1$–$C_4$) alkyl; and a halo-substituted, nitro-substituted, or un-substituted moiety selected from the group consisting of 2-thienyl, 3-thienyl, 2-furyl, 3-furyl, 2-pyridyl, 3-pyridyl, and 4-pyridyl. A cannot be $R^4$S- where $R^4$ is any moiety. Examples of heterocyclic R substituents are furyl, thienyl, pyridyl, and the like.

The iodopropargyl compounds, i.e., those wherein X is I, are preferred. The 5-one compounds, i.e., those wherein Y is O, are also preferred.

As stated above, compositions comprising a compound according to formula I and either an agronomically acceptable carrier, a cosmetic agent, a cutting oil, a soap or synthetic detergent, a stabilizer, a film forming material, or the like have a wide range of utility for protecting against or controlling microorganisms from a wide variety of classes including fungus, bacteria, algae, viruses and yeasts. The preferred utilities of the compositions are to protect wood, paint, adhesive, glue, paper, textile, leather, plastics, cardboard, lubricants, cosmetics, food, caulking, feed and industrial cooling water from microorganisms.

The following lists specific industries and applications of the compounds or compositions.

| Industry | Application |
| --- | --- |
| Adhesives, Sealants | Adhesives |
|  | Caulks |
|  | sealants |

| Industry | Application |
|---|---|
| agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | Cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| formulated household products | fabric softeners |
| | polishes |
| | waxes |
| | hand dish detergents |
| | raw materials |
| | liquid detergents |
| | hand soaps |
| Industrial processing, misc | electrodeposition paint, baths, rinses. |
| | electrodeposition pre-treatment, post rinses |
| | Industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry wash water |
| | sanitizers-laundry |
| Leather, Leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| metalworking & related app's | cutting fluids |
| | Metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings coating | emulsions |
| | paints |
| Paper and wood pulp, their products | absorbant materials of paper and wood pulp |
| | packaging materials of paper and wood pulp |
| | paper products |
| | paper treatment |
| | soap wrap |
| | wood pulp |
| | wood pulp products |
| paper mill | paper mill slimicides |
| | pulp and paper slurries |
| Petroleum refining, fuels | aviation fuels (jet fuel, aviation gas) |
| | crude oils |
| | burner, diesel and turbine fuel oils |
| | coal slurries |
| | diesel fuel additives |
| | diesel fuels |
| | fuels |
| | gasoline |
| | heating oils |
| | hydrocarbons |
| | Kerosene |
| | liquefied petroleum gas |
| | petrochemical feedstocks |
| | petroleum products, storage, transportation and production |
| | recycled petroleum products |
| | residual fuel oils |
| | turbine oils |
| Photographic Chemicals and process | Photographic processing - wash water, rinses |
| | photoprocessing |
| | Photoplate processing chemicals (developers, stabilizers etc) |
| Printing | Fountain solutions (printing) |
| | Ink components (pigments, resins, solvents, etc) |
| | Inks |
| sanitizers (active) | sanitizers |
| | sanitizers-dairy |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents |
| | household cleaners |
| | industrial cleaners |
| | liquid soaps |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |

| Industry | Application |
|---|---|
| Textile processing | woven fabrics<br>yarn<br>dye fixatives<br>dyes<br>fiber lubricants<br>hand modifiers<br>sizes<br>Textile processing fluids |
| Therapeutic (active or preservative) | animal health/veterinary<br>aquaculture<br>dental<br>human health<br>pharmaceutical/therapeutic |
| water purification | charcoal beds<br>deionization resins<br>filters<br>membranes<br>reverse osmosis membranes<br>ultrafilters<br>Water purification<br>water purificiation pipes, tubing |
| wood applications | lazures (wood stains)<br>wood<br>wood products |
| Miscellaneous | alcohols<br>bedding incorporating water or gels<br>ceramic<br>contact lens cases-leaching<br>electronic circuitry<br>electronics chemicals<br>enzymes-food production<br>enzymes<br>enzymes-industrial<br>gel cushions<br>marine antifoulants<br>mildewcides<br>wood<br>plastics<br>laundry<br>mining<br>natural rubber latex<br>oil field injection waters including enhanced recover injection fluids, drilling, fracturing and completion fluids<br>pipes<br>plastics<br>polymer systems<br>polymers and resins (synthetic and natural)<br>reagent preservation<br>rubber<br>rubber products<br>skin remover<br>solid protective/decorative films<br>stains<br>swimming pools<br>waste treatment<br>water beds |

The amounts of the compound to be used depend on the application. The useful amounts for a particular application are similar to amounts used for other microbiocide compounds.

The compound can be used in combination with other microbicides. The term "microbicide" is considered equivalent to "antimicrobial" as used herein.

Compounds of formula I can be prepared by a variety of methods. One suitable method comprises reacting a compound of the formula

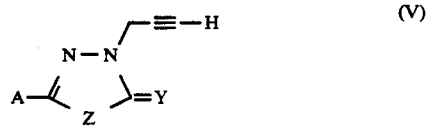

with an iodinating or brominating agent.

Suitable iodinating or brominating agents include, for example, iodine, bromine, an iodine-amino compound such as morpholineiodine complex, morpholine-bromine complex, N-bromosuccinimide ("NBS") and N-iodosuccinimide ("NIS"), the latter being the most preferred.

When an iodine, bromine, or iodo-amino compound is used, base should also be used, preferably sodium or potassium hydroxide, and solvent such as methanol, ethanol, and aqueous ethanol should also be used.

When NIS or NBS is used, a catalyst such as, for example, silver nitrate, or the like, should be used in presence of solvent such as acetone, methyl ethyl ketone, tetrahydrofuran, and the like.

Reaction times of about 20 minutes to about 24 hours have been utilized successfully with reaction temperatures of about 0° C. to about 25° C.

Suitable methods of application of compounds of formula I to control fungi, bacteria, algae, viruses, yeasts, and the like are in amounts and with carriers, etc., as well known in the art.

The following examples are presented to illustrate a few embodiments of the invention. All parts and percentages are by weight unless otherwise indicated.

EXAMPLES

Some representative compounds the invention are the following:

| Compound # | |
|---|---|
| 1. | 2-(4-chlorophenyl)-4-(3-iodopropargyl)-1,3,4-oxadiazolin-5-one |
| 2. | 2-(2-methylphenyl)-4-(3-iodopropargyl)-1,3,4-oxadiazolin-5-one |
| 3. | 2-(4-methylphenyl)-4-(3-iodopropargyl)-1,3,4-oxadiazolin-5-one |
| 4. | 2-(3-methylphenyl)-4-(3-iodopropargyl)-1,3,4-oxadiazolin-5-one |
| 5. | 2-(2-chlorophenyl)-4-(3-iodopropargyl)-1,3,4-oxadiazolin-5-one |
| 6. | 2-(3-chlorophenyl)-4-(3-iodopropargyl)-1,3,4-oxadiazolin-5-one |
| 7. | 2-(2-thienyl)-4-(3-iodopropargyl)-1,3,4-oxadiazolin-5-one |
| 8. | 2-n-propyl-4-(3-iodopropargyl)-1,3,4-oxadiazolin-5-one |
| 9. | 2-(4-nitrophenyl)-4-(3-iodopropargyl)-1,3,4-oxadiazolin-5-one |
| 10. | 2-(3-nitrophenyl)-4-(3-iodopropargyl)-1,3,4-oxadiazolin-5-one |
| 11. | 2-(2-nitrophenyl)-4-(3-iodopropargyl)-1,3,4-oxadiazolin-5-one |
| 12. | 2-(4-trifluoromethylphenyl)-4-(3-iodopropargyl)-1,3,4-oxadiazolin-5-one |
| 13. | 2-(2-methoxyphenyl)-4-(3-iodopropargyl)-1,3,4-oxadiazolin-5-one |
| 14. | 2-(4-methoxyphenyl)-4-(3-iodopropargyl)-1,3,4-oxadiazolin-5-one |
| 15. | 2-(3-methoxyphenyl)-4-(3-iodopropargyl)-1,3,4-oxadiazolin-5-one |
| 16. | 2-(4-bromophenyl)-4-(3-iodopropargyl)-1,3,4-oxadiazolin-5-one. |
| 17. | 2-(2-fluorophenyl)-4-(3-iodopropargyl)-1,3,4-oxadiazolin-5-one |
| 18. | 2-(2-furyl)-4-(3-iodopropargyl)-1,3,4-oxadiazolin-5-one |
| 19. | 1-(3-iodopropargyl)-3-(4-methylphenyl)-4-ethyl-1,2,4- |

| Compound # | |
|---|---|
| 20. | 1-(3-iodopropargyl)-3-(4-chlorophenyl)-4-ethyl-1,2,4-triazolin-5-one |
| 21. | 1-(3-iodopropargyl)-3-phenyl-4-ethyl-1,2,4-triazolin-5-one |
| 22. | 1-(3-iodopropargyl)-3-(4-nitrophenyl)-4-ethyl-1,2,4-triazolin-5-one |
| 23. | 1-(3-iodopropargyl)-3-(4-methoxyphenyl)-4-ethyl-1,2,4-triazolin-5-one |
| 24. | 1-(3-iodopropargyl)-3-(2-thienyl)-4-ethyl-1,2,4,-triazolin-5-one |
| 25. | 1-(3-iodopropargyl)-3-(3-methylphenyl)-4-ethyl-1,2,4-triazolin-5-one |
| 26. | 1-(3-iodopropargyl)-3-(2-methylphenyl)-4-ethyl-1,2,4-triazolin-5-one |
| 27. | 1-(3-iodopropargyl)-3-(3-fluorophenyl)-4-ethyl-1,2,4-triazolin-5-one |
| 28. | 1-(3-iodopropargyl)-3-(1-naphthyl)-4-ethyl-1,2,4-triazolin-5-one |
| 29. | 1-(3-iodopropargyl)-3-(2-naphthyl)-4-ethyl-1,2,4-triazolin-5-one |
| 30. | 1-(3-iodopropargyl)-3-(4-bromophenyl)-4-ethyl-1,2,4-triazolin-5-one |
| 31. | 1-(3-iodopropargyl)-3-(2-fluorophenyl)-4-ethyl-1,2,4-triazolin-5-one |
| 32. | 1-(3-iodopropargyl)-3-(4-fluorophenyl)-4-ethyl-1,2,4-triazolin-5-one |
| 33. | 1-(3-iodopropargyl)-3-(3-pyridyl)-4-ethyl-1,2,4-triazolin-5-one |
| 34. | 1-(3-iodopropargyl)-3-(2-methoxyphenyl)-4-ethyl-1,2,4-triazolin-5-one |
| 35. | 1-(3-iodopropargyl)-3-(3-nitrophenyl)-4-ethyl-1,2,4-triazolin-5-one |
| 36. | 1-(3-iodopropargyl)-3-(3-chlorophenyl)-4-ethyl-1,2,4-triazolin-5-one |
| 37. | 1-(3-iodopropargyl)-3-(3-bromophenyl)-4-ethyl-1,2,4-triazolin-5-one |
| 38. | 1-(3-iodopropargyl)-3-(3-methoxyphenyl)-4-ethyl-1,2,4-triazolin-5-one |
| 39. | 1-(3-iodopropargyl)-3-(3-ethoxyphenyl)-4-ethyl-1,2,4-triazolin-5-one |
| 40. | 1-(3-iodopropargyl)-3-(4-methylphenyl)-4 n-butyl-1,2,4-triazolin-5-one |
| 41. | 1-(3-iodopropargyl)-3-(4-methylphenyl)-4-i-propyl-1,2,4-triazolin-5-one |
| 42. | 1-(3-iodopropargyl)-3-n-propyl-4-ethyl-1,2,4-triazolin-5-one |
| 43. | 1-(3-iodopropargyl)-3-(4-chlorophenyl)-4-phenyl-1,2,4-triazolin-5-one |
| 44. | 1-(3-iodopropargyl)-3-(2-chlorophenyl)-4-ethyl-1,2,4-triazolin-5-one |
| 45. | 1-(3-iodopropargyl)-3-(4-chlorophenyl)-4-(4-chlorophenyl)-1,2,4-triazolin-5-one |
| 46. | 1-(3-iodopropargyl)-3-(4-chlorophenyl)-4-(4-methylphenyl)-1,2,4-triazolin-5-one |
| 47. | 1-(3-iodopropargyl)-3-methyl-4-phenyl-1,2,4-triazolin-5-one |
| 48. | 1-(3-iodopropargyl)-3-methyl-4-(4-chlorophenyl)-1,2,4-triazolin-5-one |
| 49. | 1-(3-iodopropargyl)-4-(4-chlorophenyl)-1,2,4-triazoline-5-one |
| 50. | 1-(3-iodopropargyl)-4-phenyl-1,2,4-triazolin-5-one |
| 51. | 1-(3-iodopropargyl)-3-(4-bromophenyl)-4-methyl-1,2,4-triazolin-5-one |
| 52. | 1-(3-iodopropargyl)-3-(4-chlorophenyl)-4-methyl-1,2,4-triazolin-5-one |
| 53. | 1-(3-iodopropargyl)-3-(4-fluorophenyl)-4-methyl-1,2,4-triazolin-5-one |
| 54. | 1-(3-iodopropargyl)-3-(3-chlorophenyl)-4-methyl-1,2,4-triazolin-5-one |
| 55. | 1-(3-iodopropargyl)-3-(3-bromophenyl)-4-methyl-1,2,4-triazolin-5-one |
| 56. | 1-(3-iodopropargyl)-3-(3-fluorophenyl)-4-methyl-1,2,4-triazolin-5-one |
| 57. | 1-(3-iodopropargyl)-3-(2-fluorophenyl)-4-methyl-1,2,4-triazolin-5-one |
| 58. | 1-(3-iodopropargyl)-3-t-butyl-4-phenyl-1,2,4-triazolin-5-one |
| 59. | 2-phenyl-4-iodopropargyl-1,3,4-thiadiazolin-5-one |

Table (1) shows the structures and the physical data of these representative compounds.

TABLE 1

Physical Data

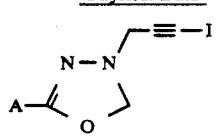

(II)

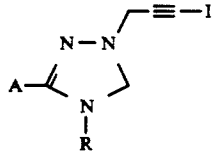

(III)

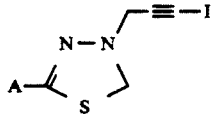

(IV)

| NO. | Formula | A | R | Melting Point | NMR Chemical Shifts (ppm) |
|---|---|---|---|---|---|
| 1. | II | 4-Cl-ph | — | 151–152° C. | |
| 2. | II | 2-Me-ph | — | 152–154° C. | |
| 3. | II | 4-Me-ph | — | 174–175° C. | |
| 4. | II | 3-Me-ph | — | 114–115° C. | |
| 5. | II | 2-Cl-ph | — | 104–107° C. | |
| 6. | II | 3-Cl-ph | — | 124–126° C. | |
| 7. | II | 2-thiophene | — | 149–151° C. | |
| 8. | II | n-propyl | — | 42–46° C. | 4.60(2H, s, CH$_2$), 2.55 (2H, t, CH$_2$), 1.74(2H, m |

TABLE 1-continued

Physical Data

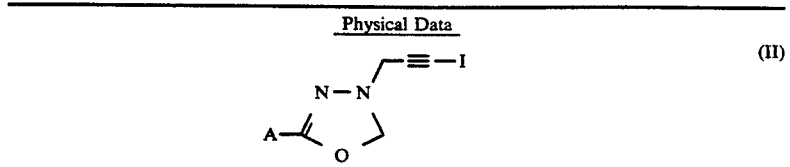
(II)

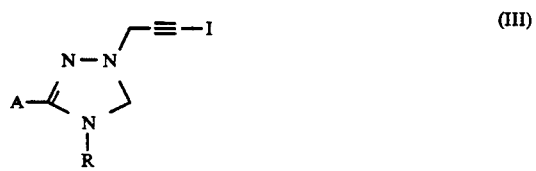
(III)

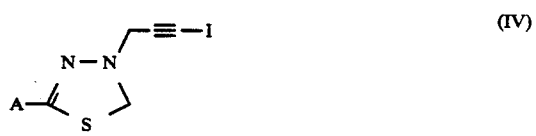
(IV)

| NO. | Formula | A | R | Melting Point | NMR Chemical Shifts (ppm) |
|---|---|---|---|---|---|
| | | | | | $CH_2$), 1.02(3H, t, $CH_3$) |
| 9. | II | 4-$NO_2$-ph | — | 176–178° C. | |
| 10. | II | 3-$NO_2$-ph | — | 99.5–102° C. | |
| 11. | II | 2-$NO_2$-ph | — | 116–120° C. | |
| 12. | II | 4-$CF_3$-ph | — | 144–147° C. | |
| 13. | II | 2-MeO-ph | — | 115–117° C. | |
| 14. | II | 4-MeO-ph | — | 171–173° C. | |
| 15. | II | 3-MeO-ph | — | 128–130° C. | |
| 16. | II | 4-Br-ph | — | 159–162° C. | |
| 17. | II | 2-F-ph | — | 139–142° C. | |
| 18. | II | furyl-2 | — | 140–142° C. | |
| 19. | III | 4-Me-ph | Et | 141–145° C. | |
| 20. | III | 4-Cl-ph | Et | 115–120° C. | |
| 21. | III | ph | Et | 144–148° C. | |
| 22. | III | 4-$NO_2$-ph | Et | 184–187° C. | |
| 23. | III | 4-OMe-ph | Et | oil | 7.20(4H, aromatic H), 4.75(2H, s, $CH_2$) 3.84 (3H, s, $CH_3$), 3.75 (2H, q, $CH_2$) 1.28 (3H, t, $CH_3$) |
| 24. | III | 2-thiophene | Et | 134–136° C. | |
| 25. | III | 3-Me-ph | Et | oil | 7.34(4H, m, arom. H), 4.78(2H, s, $CH_2$), 3.80 (2H, q, $CH_2$), 2.40 (3H, s, $CH_3$), 1.25 (3H, t, $CH_3$) |
| 26. | III | 2-Me-ph | Et | oil | 7.35(4H, m, arom. H), 4.80(2H, s, $CH_2$), 3.56 (2H, q, $CH_2$), 2.29 (3H, s, $CH_3$) 1.12 (3H, t, $CH_3$) |
| 27. | III | 2-F-ph | Et | 104–107° C. | |
| 28. | III | 1-naphthyl | Et | 148–152° C. | |
| 29. | III | 2-naphthyl | Et | 63–70° C. | |
| 30. | III | 4-Br-ph | Et | 125–126° C. | |
| 31. | III | 2-F-ph | Et | 121–124° C. | |
| 32. | III | 4-F-ph | Et | 108–111° C. | |
| 33. | III | 3-pyridyl | Et | 129–131° C. | |
| 34. | III | 3-OMe-ph | Et | 127–130° C. | |
| 35. | III | 3-$NO_2$-ph | Et | 153–158° C. | |
| 36. | III | 3-Cl-ph | Et | — | 7.60(4H, m, arom. H), 4.81(2H, s, $CH_2$), 3.85 (2H, q, $CH_2$), 1.32 (3H, t, $CH_3$) |
| 37. | III | 3-Br-ph | Et | — | 7.80 to 7.40 (4H, m, arom. H), 4.80 (2H, s, $CH_2$), 3.84 (2H, q, $CH_2$), 1.30(3H, t, ($CH_3$) |
| 38. | III | 3-OMe-ph | Et | — | 7.50 to 7.00(4H, m, arom. H), 4.80 (2H, s, $CH_2$), 3.85(4H, m, $CH_3$ & $CH_2$), 1.30 (3H, t, $CH_3$) |
| 39. | III | 3-OEt-ph | Et | — | 7.50 to 7.00 (4H, m, arom. H), 4.80 |

TABLE 1-continued

Physical Data (II)

$$\text{A}-\underset{\text{O}}{\overset{\text{N}-\text{N}}{\diagdown}}\text{—CH}_2\text{—C}\equiv\text{C—I}$$

(III)

$$\text{A}-\underset{\underset{\text{R}}{\text{N}}}{\overset{\text{N}-\text{N}}{\diagdown}}\text{—CH}_2\text{—C}\equiv\text{C—I}$$

(IV)

$$\text{A}-\underset{\text{S}}{\overset{\text{N}-\text{N}}{\diagdown}}\text{—CH}_2\text{—C}\equiv\text{C—I}$$

| NO. | Formula | A | R | Melting Point | NMR Chemical Shifts (ppm) |
|---|---|---|---|---|---|
|  |  |  |  |  | (2H, s, CH$_2$), 4.10 |
|  |  |  |  |  | (2H, q, CH$_2$), 3.84 |
|  |  |  |  |  | (2H, q, CH$_2$), 1.46 |
|  |  |  |  |  | (3H, t, CH$_3$), 1.26 |
|  |  |  |  |  | (3H, t, CH$_3$) |
| 40. | III | 4-Me-ph | n-Bu | — | 7.40(4H, q, arom. H), |
|  |  |  |  |  | 4.78(2H, s, CH$_2$), 3.80 |
|  |  |  |  |  | (2H, t, CH$_2$), 2.44 |
|  |  |  |  |  | (3H, s, CH$_3$), 1.62 |
|  |  |  |  |  | (2H, m, CH$_2$), 1.30 |
|  |  |  |  |  | (2H, m, CH$_2$), |
|  |  |  |  |  | 0.85(3H, t, CH$_3$) |
| 41. | III | 4-Me-ph | i-pro | — | 7.38(4h, q, arom. H), 4.75 |
|  |  |  |  |  | (2H, s, CH$_2$), 4.26 |
|  |  |  |  |  | (1H, m, CH), 2.45 |
|  |  |  |  |  | (3H, s, CH$_3$), 1.55 |
|  |  |  |  |  | (6H, d, 2-CH$_3$) 1.55 |
|  |  |  |  |  | (6H, d, 2-CH$_3$) |
| 42. | III | n-prop | Et | 89–93° C. |  |
| 43. | III | 4-Cl-ph | ph | 193–195° C. |  |
| 44. | III | 2-Cl-ph | Et | 86–89° C. |  |
| 45. | III | 4-Cl-ph | 4-Cl-ph | 171–177° C. |  |
| 46. | III | 4-Cl-ph | 4-Me-ph | 179–183° C. |  |
| 47. | III | Me | ph | 179–182° C. |  |
| 48. | III | Me | 4-Cl-ph | 129–131° C. |  |
| 49. | III | H | 4-Cl-ph | 147–149° C. |  |
| 50. | III | H | ph | 192–193° C. |  |
| 51. | III | 4-Br-ph | Me | 145–150° C. |  |
| 52. | III | 4-Cl-ph | Me | 148–152° C. |  |
| 53. | III | 4-F-ph | Me | 122–125° C. |  |
| 54. | III | 3-Cl-ph | Me | 78–82° C. |  |
| 55. | III | 3-Br-ph | Me | 89–94° C. |  |
| 56. | III | 3-F-ph | Ne | 124–129° C. |  |
| 57. | III | 2-F-ph | Me | 121–126° C. |  |
| 58. | III | t-Butyl | ph | 170–174° C. |  |
| 59. | IV | ph | — | 117–119° C. |  |
| 60 | II | 1-naphthyl | — | 167–169° C. |  |
| 61 | II | Me | — | 90–96° C. |  |
| 62 | II | n-C$_{17}$H$_{35}$ | — | 41–46° C. |  |
| 63 | II | n-C$_4$H$_9$ | — | oil | 4.60(2H, s, CH$_2$), 2.60 |
|  |  |  |  |  | (2H, t, CH$_2$), 1.70 |
|  |  |  |  |  | (2H, m, CH$_2$), 1.42 |
|  |  |  |  |  | (2H, m, CH$_2$), 0.95 |
|  |  |  |  |  | (3H, t, CH$_3$) |
| 64 | II | t-C$_4$H$_9$ | — | 90–93° C. |  |
| 65 | II | 3-Br-ph | — | 127–129° C. |  |
| 66 | II | 4-F-ph | — | 127–129° C. |  |
| 67 | II | 3-F-ph | — | 127–129° C. |  |
| 68 | II | ph | — | 137–139° C. |  |
| 69 | II | 2-EtO-ph | — | 138–142° C. |  |
| 70 | II | 3-EtO-ph | — | 129–132° C. |  |
| 71 | II | 2-Cl, 4-NO$_2$-ph | — | 161–166° C. |  |
| 72 | II | 4-ph-ph | — | 183–186° C. |  |
| 73. | II | 3,5-(OMe)$_2$-ph | — | 161–165° C. |  |
| 74. | II | 2,5-(OMe)$_2$-ph | — | 144–147° C. |  |
| 75. | II | 3,4,5-(OMe)$_3$-ph | — | 135–137° C. |  |

TABLE 1-continued

Physical Data (II)

A—C(=N—N)—CH2—O ring with N-CH2-C≡C-I (III)

A—C(=N—N)—CH2—N(R) ring with N-CH2-C≡C-I (IV)

A—C(=N—N)—CH2—S ring with N-CH2-C≡C-I

| NO. | Formula | A | R | Melting Point | NMR Chemical Shifts (ppm) |
|---|---|---|---|---|---|
| 76. | II | 2,5-Cl$_2$-ph | — | 121–123° C. | |
| 77. | II | n-Heptyl | — | Oil | 4.62(2H, s, CH$_2$), 2.58(2H, t, CH$_2$), 1.70(2H, m, CH$_2$). 1.32(12H, m 4CH$_2$), 0.90(3H, t, CH$_3$) |
| 78. | III | t-Bu | 3-F-ph | 151–160° C. | |
| 79. | III | t-Bu | Me | Oil | 4.72(2H, s, CH$_2$), 3.42(3H, s, CH$_3$), 1.40(9H, s, 3CH$_3$) |
| 80. | III | t-Bu | Et | Oil | 4.70(2H, s, CH$_2$), 3.88(2H, q, CH$_2$), 1.38(12H, m, 4CH$_3$) |
| 81. | III | Me | Et | Oil | 4.68(2H, s, CH$_2$), 3.72(2H, q, CH$_2$), 2.26(3H, s, CH$_3$), 1.30(3H, t, CH$_3$) |
| 82. | III | n-Bu | Et | Oil | 4.82(2H, s, CH$_2$), 3.70(2H, q, CH$_2$), 2.40(2H, t, CH$_2$), 1.66(2H, m, CH$_2$), 1.38(5H, m), 0.98(3H, t, CH$_3$) |
| 83. | III | t-Bu | 3-MeO-ph | 168–170° C. | |
| 84. | III | n-Pr | 4-Cl-ph | 50–56° C. | |
| 85. | III | n-Pr | ph | 106–112° C. | |
| 86. | III | t-Bu | 4-Cl-ph | 168–171° C. | |
| 87. | III | Me | 4-Me-ph | 166–170° C. | |
| 88. | III | Me | 4-MeO-ph | 200–203° C. | |
| 89. | III | n-Pr | 4-MeO-ph | Oil | 7.22(4H, q, arom. H), 4.76(2H, s, CH$_2$), 3.85(3H, s, CH$_3$), 2.40(2H, t, CH$_2$), 1.58(2H, m, CH$_2$), 0.90(3H, t, CH$_3$) |
| 90. | III | n-Pr | 3-MeO-ph | 109–112° C. | |
| 91. | III | n-Pr | 2-MeO-ph | Oil | 7.55–7.02(4H, m, arom. H), 4.78(2H, s, CH$_2$), 3.86(3H, s, CH$_3$), 2.32(2H, q, CH$_2$), 1.60(2H, m, CH$_2$), 0.90(3H, t, CH$_3$) |
| 92. | III | Me | n-Hexyl | Oil | 4.70(2H, s, CH$_2$), 3.60(2H, t, CH$_2$), 2.26(3H, s, CH$_3$), 1.64(2H, m, CH$_2$), 1.34(6H, m, 3CH$_2$), 0.91(3H, t, CH$_3$) |
| 93. | III | Me | Benzyl | 170–172° C. | |
| 94. | III | Me | Cyclohexyl | 103–106° C. | |
| 95. | III | H | 3-Cl-ph | 112–115° C. | |
| 96. | III | H | 3-Me-ph | 153–156° C. | |
| 97. | III | H | 2-Me-ph | 132–134° C. | |
| 98. | III | H | 2-Cl-ph | 139–140° C. | |
| 99. | III | H | 4-Me-ph | 165–170° C. | |

TABLE 1-continued

Physical Data

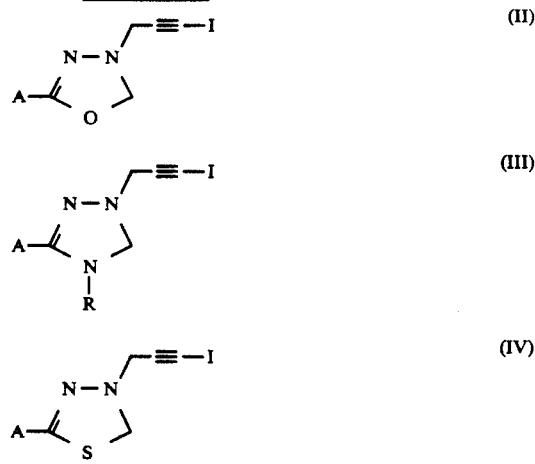

| NO. | Formula | A | R | Melting Point | NMR Chemical Shifts (ppm) |
|---|---|---|---|---|---|
| 100. | III | H | n-Bu | 66–70° C. | |
| 101. | III | H | Et | Oil | 7.42(1H, s)<br>4.64(2H, s, CH$_2$),<br>3.70(2H, q, CH$_2$),<br>1.34(3H, t, CH$_3$) |
| 102. | III | H | 4-F-ph | 124–127° C. | |
| 103. | III | H | 4-MeO-ph | 117–120° C. | |
| 104. | III | H | 4-NO$_2$-ph | 165–166° C. | |
| 105. | III | H | 4-Br-ph | 175–177° C. | |
| 106. | III | H | 2,4-Cl$_2$-ph | 148–151° C. | |
| 107. | III | H | 3,4-Cl$_2$-ph | 160–161° C. | |
| 108. | III | H | 3,5-Cl$_2$-ph | 101–105° C. | |
| 109. | III | H | 3-F-ph | 172–175° C. | |
| 110. | III | H | 3-Br-ph | 105–110° C. | |
| 111. | III | H | 2-F-ph | 115–120° C. | |
| 112. | III | H | Cyclohexyl | 118–122° C. | |
| 113. | III | H | Benzyl | 119–124° C. | |
| 114. | III | H | n-Hexyl | Oil | 7.45(1H, s, olefinic H),<br>4.74(2H, s, CH$_2$),<br>3.64(2H, t, CH$_2$),<br>1.72(2H, m, CH$_2$),<br>1.35(6H, m, 3CH$_2$).<br>0.90(3H, t, CH$_3$) |
| 115. | III | H | 2,6-Cl$_2$-ph | 115–120° C. | |
| 116. | III | H | 3,5-Me$_2$-ph | 80–85° C. | |
| 117. | III | H | 2,4-Me$_2$-ph | 119–124° C. | |
| 118. | III | H | 4-Et-ph | 129–132° C. | |
| 119. | III | H | 3-Et-ph | 82–87° C. | |
| 120. | III | H | n-Octyl | Oil | 7.44(1H, s, olefinic H),<br>4.72(2H, s, CH$_2$),<br>3.62(2H, t, CH$_2$),<br>1.72(2H, m, CH$_2$),<br>1.30(10H, m, 5CH$_2$),<br>0.90(3H, t, CH$_3$) |
| 121. | III | H | n-Dodecyl | 50–52° C. | |

EXAMPLE 1

Preparation of 2-(4-Chlorophenyl)-4-3-Iodopropargyl)-1,3,4-Oxadiazolin-5-one (Compound #1)

To the suspension of 4-chlorobenzhydrazide (8.53 g, 0.05 mole) in methylene chloride (100 ml), equipped with a magnetic stirring bar, a nitrogen inlet, a dropping funnel, and an outlet connected to diluted base solution for trapping the HCl gas, was dropwise added trichloromethyl chloroformate (5.94 g, 0.03 mole). After addition, the reaction mixture was heated to reflux for 2 hr. The reaction was cooled down to room temperature and poured into a mixture of water (500 ml) and hexane (200 ml) and stirred for 10 to 20 min. The resultant precipitate was collected by suction-filtration and was washed with hexane to give a solid product. The product was dried in air at room temperature overnight yielding 5.5 g (60% yield) of 2-(4-chlorophenyl)-1,3,4-oxadiazolin-5-one as a solid, m.p.=225°–227° C. NMR and IR spectra showed the desired structure. Without further purification, this product was subjected to the next step.

To the suspension of 2-(4-chlorophenyl)-1,3,4-oxadiazolin-5-one (2 g, 0.01 mole) in acetone (50 ml) was added potassium carbonate (2 g, 0.015 mole), followed by propargyl bromide (1.6 g of 80% in toluene, 0.0106 mole) with magnetic stirring under nitrogen for 3 hr. The reaction mixture was cooled down to room temperature. The suspension was filtered by suction-filtration and the solid was washed with acetone. The filtrate was concentrated to about 10 ml and was poured into water (200 ml). The resultant precipitate was collected by suction-filtration and washed with water and hexane affording 0.85 g (36% yield), after drying in air, of 2-(4-chlorophenyl)-4-propargyl-1,3,4-oxadiazolin-5-one as a solid. m.p.=125°-127° C. NMR and IR spectra showed the desired structure. Without further purification, this compound was subjected to the next step.

To the suspension of 2-(4-chlorophenyl)-4-propargyl-1,3,4-oxadiazolin-5-one (0.6 g, 0.00256 mole) in acetone (20 ml) with magnetic stirring at room temperature was added N-iodosuccinimide (0.6 g, 0.00266 mole), followed by silver nitrate (0.040 g, 0.00024 mole). The reaction mixture was stirred at room temperature for one hour. The suspension was filtered gravitationally and the solid was rinsed with acetone. The filtrate was poured into water (300 ml). The resultant precipitate was collected by suction-filtration and air-dried to give 0.8 g (92% yield), of 2-(4-chlorophenyl)-4-(3-iodopropargyl)-1,3,4-oxadiazolin-5-one as a solid. m.p.=151°-152° C. The proton NKM spectrum was consistent with the desired structure.

EXAMPLE 2

1-(3-Iodopropargyl)-3-(4-chlorophenyl)-4-ethyl-1,2,4-triazolin-5-one (Compound #20)

To a suspension of 4-chlorobenzhydrazide (98.5 g, 0.05 mole) in tetrahydrofuran (100 ml) at room temperature ethylisocyanate (4.2 g, 0.05 mole) was added slowly with magnetic stirring. The reaction was slightly exothermic and the reaction mixture turned to a thick paste. Stirring was continued an additional 30 min after which the solid was collected by suction-filtration and washed with a small amount of tetrahydrofuran and dried to provide 11.6 g (96.6% yield), of 1-(4chlorobenzoyl)-4-ethyl semicarbazide as a white solid., m.p.=242°-243° C. The above semicarbazide (10 g, 0.0414 mole) was dissolved in 1N sodium hydroxide solution (100 ml) and was refluxed with stirring for 16 hr. The solution was cooled down to about 10° C. by an ice bath and was neutralized by conc. hydrogen chloride until pH 2. The resultant white solid was collected by suction-filtration and washed with water to give 8.65 g (93.5% yield) of 3-(4-chlorophenyl)-4-ethyl-1,2,4-triazolin-5-one as a white solid. m.p.=190°-197° C. A proton NMR spectrum was consistent with the desired structure.

To the solution of 3-(4-chlorophenyl)-4-ethyl-1,2,4-triazolin-5-one (2.23 g, 0.01 mole) in dry acetone (40 ml) was added, at room temperature, potassium carbonate (1.67 g, 0.012 mole) followed by propargyl bromide (1.8 g of 80% in toluene, 0.012 mole). The reaction mixture was then refluxed with stirring for 6 hr. The mixture was cooled down to room temperature and solvent was evaporated to give a residue. The product was purified by crystallization from hexane/ether, affording 1.8 g (69.2% yield) of 1-propargyl-3-(4-chlorophenyl)-4-ethyl-1,2,4-triazolin-5-one as a white solid. m.p.=115°-119° C. A proton NMR spectrum was consistent with the desired structure.

To the solution of 1-propargyl-3-(4-chlorophenyl)-4-ethyl-1,2,4-triazolin-5-one (1.0 g , 3.82 mmole) in dry acetone (20 ml) was added N-iodosuccinimide (0.95 g, 4.2 mmole), followed by silver nitrate (50 mg, 0.29 mmole) with magnetic stirring at room temperature. The reaction mixture was stirred for 1 hr. The resultant suspension was filtered and the filtrate was poured into water (250 ml). A yellowish white solid slowly precipitated out and was collected by suction-filtration and washed with water to give 1.12 g (76% yield) of 1-(3-iodopropargyl)-3-(4-chloro-phenyl)-4-ethyl-1,2,4-triazolin-5-one as a light yellow solid. m.p.=115°-120° C. A proton NMR spectrum was consistent with the desired compound.

EXAMPLE 3

Preparation of 2-phenyl-4-iodopropargyl-1,3,4-thiadiazolin-5-one (Compound 59)

A. Preparation of Thiobenzhydrazide

A cold solution of S-(thiobenzoly)thioglycolic acid (12.25 g, 57.6 mmole) in 1N NAOH (60 ml, 60 mmole NAOH) was slowly added to a solution of hydrazine monohydrate (6 g, 123.8 mmole) in 5 ml of water at about 5° C. with magnetic stirring. After the addition, the resultant yellow suspension was stirred at room temperature for one hour. The mixture was cooled down to 5° C. and was acidified with conc. HCl until pH=6. The yellow solid was collected by suction-filtration and was washed with water to afford 3.70 g, after drying in air. m.p.=66°-68° C.

B. Preparation of 2-phenyl-1,3,4-thiadiazolin-5-one

To a solution of thiobenzhydrazide (3.7 g, 24.34 mmole) in methylene chloride (50 ml), equipped with magnetic stirrer, nitrogen inlet, and an outlet connected to a trap containing a diluted NAOH solution, was added trichloromethyl chloroformate (4 g, 20.2 mmole). The reaction mixture was stirred at room temperature for one hour. The mixture was diluted with methylene chloride (100 ml) and washed with water (3×50 ml) and brine. The organic layer was dried over MgSO$_4$. After the drying agent was filtered off the filtrate was concentrated to a residue. The residue was triturated with hexane and the solid product was collected by suction-filtration to give 3.7 g as a powder. m.p.=140°-143° C.

C. Preparation of 2-phenyl-4-propargyl-1,3,4-thiadiazolin-5-one

To the solution of 2-phenyl-1,3,4-thiadiazolin-5-one (3 g, 16.85 mmole) in dry acetone (30 ml) under nitrogen with magnetic stirring was added potassium carbonate (3 g, 22 mmole), followed by propargyl bromide (3 g, 80% in toluene, 20 mmole) at room temperature. The mixture was refluxed for one hour. The reaction mixture was cooled down to room temperature and the solid was filtered off by suction-filtration. The filtrate was diluted with ether (200 ml) and washed with water (2×50 ml) and brine. The organic layer was dried over sodium sulfate. After the drying agent was filtered off the filtrate was concentrated to about 5 ml. Hexane was added to precipitate out the product. The product was collected by suction-filtration and washed with a little hexane to afford 2 g of 2-phenyl-4-propargyl-1,3,4-thiadiazolin-5-one as a powder. m.p.=73°-75° C.

D. Preparation of 2-phenyl4-iodopropargyl-1,3,4-thiadiazolin-5-one

To the solution of 2-phenyl-4-propargyl-1,3,4-thiadiazolin-5-one (1.6 g, 7.4 mmole) in dry acetone (25 ml) under nitrogen with magnetic stirring was added catalytic amount of silver nitrate 0.1 g, 0.58 mmole), followed by N-iodosuccinimide (1.85 g, 8.15 mmole).

The reaction mixture was stirred at room temperature for 20 hours. The solid was filtered off by suction-filtration through a Celite filter. The filtrate was diluted with water (200 ml) and extracted with ethyl acetate (2×100 ml). The organic layer was washed with water (2×50 ml), brine, and dried over sodium sulfate. The drying agent was filtered off and the filtrate was concentrated to give a residue. The residue was triturated with hexane and the product was collected by suction-filtration to give 1.75 g as a semicrystalline compound. m.p.=117°-119° C. Proton NMR spectrum showed the desired compound.

EXAMPLE 4

Biocidal Evaluations of Compounds

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of 500 PPM. 250 ppm, or 12 5 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8, and 4 ppm or 250, 125, 63, 32, 16, 8, 4, 2, 1, 0.5, 0.25, and 0. 12 (or 100, 50, 25, 12.5, 6.2, 3.1, 1.6, and 0.8), respectively.

Each vessel is then inoculated with a cell suspension of the appropriate test organism. Bacteria are grown in broth and fungi on agar slants and algae is grown in cooling tower media for a time and at a temperature appropriate to the species being tested. At the end of the growth period, the broth is vortexed to disperse the cells. In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound. The vessels are then incubated at the appropriate temperature. After the incubation, the vessels are examined for growth/no growth. The minimum inhibitory concentration (NEC) is defined as the lowest concentration of compound that results in complete inhibition of growth of the test organism.

The organisms tested to demonstrate biocidal activity include:

BACTERIA:
*Pseudomonas fluorescens* (Ps.fl), gram negative
*Pseudomonas aerugenosa* (Ps.ae), gram negative
*Escherichia coli* (E.c), gram negative
*Staphylococcus aureus* (S.a), gram positive
FUNGI:
*Aspergillus niger* (A.n)
*Aureobasidium pullulans* (A.p)
ALGAE:
*Chlorella pyroidenosa* (see Table 5)

TABLE 2

Biocidal Evaluation
The Result of Minimum Inhibitory Concentration (MIC) Tests

| Compound # | MIC (ppm) | | | | | |
|---|---|---|---|---|---|---|
| | Psfl | Psae | Ecol | Saur | Anig | Apul |
| 1. | >100 | >100 | >100 | >100 | <0.8 | <0.8 |
| 2. | >100 | >100 | >100 | >100 | <0.8 | <0.8 |
| 3. | 100 | >100 | >100 | >100 | >100 | <0.8 |
| 4. | 100 | >100 | >100 | >100 | 2 | <0.8 |
| 5. | >100 | >100 | >100 | 50 | <0.8 | <0.8 |
| 6. | >100 | >100 | >100 | 13 | <0.8 | <0.8 |
| 7. | 50 | 50 | 25 | 13 | <0.8 | <0.8 |
| 8. | 50 | 100 | 25 | 25 | <0.8 | <0.8 |
| 9. | >100 | >100 | >100 | >100 | <0.8 | <0.8 |
| 10. | 13 | 13 | 13 | 6 | <0.8 | <0.8 |
| 11. | 50 | 100 | >100 | 50 | <0.8 | <0.8 |
| 12. | >100 | >100 | >100 | >100 | <0.8 | <0.8 |
| 13. | >500 | >500 | >500 | >500 | 250 | 8 |
| 14. | >500 | >500 | >500 | >500 | 500 | 32 |
| 15. | >500 | 125 | >500 | >500 | 63 | <4 |
| 16. | >500 | 125 | 125 | >500 | 125 | <4 |
| 17. | >500 | >500 | >500 | >500 | 8 | <4 |
| 18. | >500 | >500 | >500 | >500 | <4 | <4 |
| 19. | 100 | 25 | 50 | 25 | <0.8 | <0.8 |
| 20. | 100 | 25 | 50 | 13 | <0.8 | <0.8 |
| 21. | >100 | 100 | 50 | 25 | <0.8 | 1.6 |
| 22. | >100 | >100 | >100 | 50 | 6.3 | 3 |
| 23. | >100 | >100 | >100 | 50 | 13 | 3 |
| 24. | >100 | >100 | >100 | 100 | 6 | 3 |
| 25. | >100 | >100 | 50 | 25 | <0.8 | <0.8 |
| 26. | >100 | >100 | 50 | 1.6 | <0.8 | 1.6 |
| 27. | 50 | 100 | >100 | 100 | 100 | 2 |
| 28. | >100 | >100 | >100 | 50 | 25 | <0.8 |
| 29. | 100 | >100 | >100 | 25 | 6.3 | <0.8 |
| 30. | >100 | >100 | 50 | 13 | <0.8 | <0.8 |
| 31. | >100 | 50 | 50 | 25 | 1.6 | <0.8 |
| 32. | 100 | 50 | 50 | 25 | <0.8 | <0.8 |
| 33. | >100 | 50 | 25 | 25 | 13 | 25 |
| 34. | >100 | >100 | >100 | 50 | 13 | 13 |
| 35. | >100 | >100 | >100 | 50 | 25 | 6 |
| 36. | 100 | >100 | >100 | >100 | <0.8 | 3 |
| 37. | 100 | 100 | >100 | 100 | <0.8 | 3 |
| 38. | >100 | 100 | >100 | >100 | 2 | 6.3 |
| 39. | >100 | >100 | >100 | >100 | 2 | 6.3 |
| 40. | >100 | >100 | >100 | >100 | 50 | 25 |
| 41. | >100 | >100 | >100 | >100 | 6.3 | 6.3 |
| 42. | >100 | >100 | >100 | 50 | 13 | 6 |
| 43. | 100 | 50 | >100 | >100 | 6 | <0.8 |
| 44. | >100 | >100 | >100 | 25 | 13 | 6 |
| 45. | >100 | >100 | >100 | >100 | >100 | >100 |
| 46. | >100 | >100 | >100 | >100 | >100 | >100 |
| 47. | 63 | 63 | 63 | 125 | 16 | 8 |
| 48. | 16 | 250 | 250 | 32 | 16 | <4 |
| 49. | 32 | 32 | 63 | 125 | 8 | <4 |
| 50. | >500 | >500 | >500 | >500 | 63 | <4 |
| 51. | 63 | 250 | 63 | 63 | 32 | <4 |
| 52. | 63 | 250 | 32 | 125 | 32 | <4 |
| 53. | 16 | 63 | 32 | 32 | <4 | <4 |
| 54. | 16 | 125 | 32 | 32 | 8 | <4 |
| 55. | 16 | 125 | 32 | 32 | 8 | <4 |
| 56. | 16 | 125 | 16 | 32 | <4 | <4 |
| 57. | 32 | 125 | 32 | 63 | 8 | <4 |
| 58. | 16 | 125 | 63 | 125 | 32 | 16 |
| 59 | 250 | >250 | >250 | 250 | <4 | 4 |
| 61 | 250 | 125 | 32 | 32 | <4 | <4 |
| 62 | 250 | 250 | 250 | 250 | <4 | <4 |
| 63 | 250 | 250 | 250 | 500 | <4 | <4 |
| 64 | 250 | 250 | 250 | 500 | <4 | <4 |
| 65 | 250 | 250 | 250 | 500 | <4 | <4 |
| 66 | 8 | 63 | 32 | 250 | <4 | <4 |
| 67 | 8 | 32 | 16 | <4 | <4 | <4 |
| 68 | 63 | 125 | >500 | 125 | <4 | 16 |
| 69 | >250 | >250 | >250 | >250 | 4 | >250 |
| 70 | 63 | 63 | >500 | 125 | <4 | — |
| 71 | 125 | 63 | >500 | 250 | 8 | — |
| 72 | >500 | >500 | >500 | >500 | >500 | >500 |
| 73 | >250 | >250 | >250 | >250 | >250 | >250 |
| 74 | >250 | >250 | >250 | >250 | 250 | >250 |
| 75 | >250 | >250 | >250 | >250 | >250 | 8 |
| 76 | >250 | >250 | >250 | >250 | 2 | 8 |
| 77 | — | 63 | >250 | 8 | <0.12 | 16 |
| 78 | | | | | | |

TABLE 2-continued

Biocidal Evaluation
The Result of Minimum Inhibitory Concentration (MIC) Tests

| Compound # | Psfl | Psae | Ecol | Saur | Anig | Apul |
|---|---|---|---|---|---|---|
| 79 | | | | | | |
| 80 | 32 | 250 | 250 | 32 | 4 | — |
| 81 | 32 | 250 | 250 | 63 | 16 | — |
| 82 | 32 | 125 | 250 | 32 | 2 | — |
| 83 | 125 | 250 | >250 | 250 | 32 | — |
| 84 | 63 | 250 | 250 | 63 | 16 | 8 |
| 85 | 125 | >250 | >250 | 63 | 16 | 8 |
| 86 | >250 | >250 | >250 | >250 | 32 | 32 |
| 87 | — | >250 | >250 | >250 | 8 | — |
| 88 | — | >250 | >250 | >250 | 63 | — |
| 89 | — | >250 | >250 | 250 | 16 | 8 |
| 90 | — | >250 | >250 | 250 | 32 | 16 |
| 91 | — | >250 | >250 | >250 | >250 | >250 |
| 92 | — | 250 | >250 | 125 | 4 | 4 |
| 93 | — | 125 | >250 | 63 | 8 | 8 |
| 94 | — | >250 | >250 | 250 | 16 | 8 |
| 95 | 32 | 250 | >250 | 63 | <0.12 | — |
| 96 | 125 | >250 | >250 | >250 | <0.12 | — |
| 97 | 63 | >250 | >250 | 125 | 4 | 4 |
| 98 | 63 | >250 | >250 | 125 | 4 | 4 |
| 99 | >250 | >250 | >250 | >250 | 8 | 4 |
| 100 | 63 | 125 | 125 | 125 | 1 | 2 |
| 101 | 63 | 250 | >250 | 63 | 16 | 8 |
| 102 | 63 | >250 | 250 | 63 | 0.25 | 2 |
| 103 | 125 | >250 | >250 | 63 | 1 | 4 |
| 104 | 63 | 125 | 125 | 63 | <0.12 | <0.12 |
| 105 | 125 | 250 | >250 | >250 | <0.12 | <0.12 |
| 106 | 125 | >250 | >250 | >250 | >250 | >250 |
| 107 | — | 125 | >250 | 250 | 2 | 16 |
| 108 | 250 | >250 | >250 | 250 | 2 | 4 |
| 109 | >250 | >250 | >250 | >250 | 32 | 16 |
| 110 | — | >250 | >250 | 125 | 2 | 1 |
| 111 | — | >250 | >250 | >250 | 2 | 1 |
| 112 | — | >250 | >250 | >250 | 2 | 2 |
| 113 | — | >250 | >250 | >250 | 0.25 | 0.25 |
| 114 | — | >250 | >250 | >250 | — | — |
| 115 | — | 250 | >250 | 250 | 32 | 16 |
| 116 | — | >250 | >250 | 250 | 16 | 8 |
| 117 | — | >250 | >250 | >250 | 32 | 8 |
| 118 | — | 63 | 250 | 250 | 16 | 8 |
| 119 | — | 125 | >250 | 250 | 32 | 8 |
| 120 | — | 63 | >250 | 4 | <0.12 | <0.12 |
| 121 | — | >250 | >250 | >250 | >250 | >250 |

EXAMPLE 5

In-Vitro Plant Fungicide Tests of Compounds

The organisms employed in the test are:
PYU   Pythium ultimum (Oomycete)
PHY   Phytophthora capsici (Oomycete)
PIR   Piricularia oryzae (Ascomycete)
FM    Cochliobolus sativus (Ascomycete)
BOC   Botrytis cinerea (Ascomycete)
FUS   Fusarium roseum (Ascomycete)
SEP   Septoria nodorum (Ascomycete)
RHI   Rhizoctonia solani (Basidiomycete)
XAN   Xanthomonas campestris (bacterium)

Methods

1. Culture maintenance: Transfers in steps 1 and 2 are done in a laminar flow hood. All 8 fungi and the bacterium used in this test are transferred and maintained on potato dextrose agar plates each week (2 plates/organism). Organisms are used when they are the following ages: a. 1 week old: PYU, PHY, RHI; b. 2 weeks old: XAN, PIR, BOC, HEL, FUS, SEP, COL, MON, CER, UST, ALT; c. 3 weeks old: PSH, VEN. Pythium ultimum and Phytophthora capsici are transferred to asparagine-sucrose broth shake cultures (ASB). Rhizoctonia solani, Fusarium roseum, and Zanthomonas campestris are mainted in yeast extract-dextrose broth (YDB) on a shaker. Culture flasks are inoculated with 6 mycelial plugs each (except for Pythium which is inoculated with only 3 plugs) taken from PDA plates. All liquid shaker cultures are used after 2 days growth.

2. Inoculum preparation. Conidia and mycelium from PIR, BOC, HEL, SEP, COL, MON, CER, PSH, UST and ALT are lightly scraped off into YDB so that mostly conidia are used as inoculum. The conidial suspension is strained through a double layer of cheesecloth to remove mycelial clumps. One plate produces enough conidia or mycelium to inoculate 100 n-d of YDB. XAN broth culture is poured (1 ml culture/100 ml broth) into YDB. PYU, PHY, RFU and FUS cultures are ground up (2-3 5 second bursts in a blender) and an but Pythium and Phytophthora are filtered through a double layer of sterile cheesecloth to remove large mycelial clumps. Ten ml of the culture solutions of R. solani and F. roseum are added to 90 ml of YSB and 10 ml of the P. capsici is added to 90 ml ASB. Two ml of the culture solution of P. ultimum is added to 98 ml of ASB. Care must be made not to overinoculate (e.g. solutions should appear fairly dear to the eye, yet when held up to light a faint cloudiness should be visible) or standards will not behave properly. The inoculum mixtures are placed in microtiter plates using a 12-tipped pipet. 175 μl (single dose) or 100 μl (dose-response test) of inoculum broth is placed in each well of the microtiter plates. The plates with inoculated media are placed in the refrigerator overnight. There are two replications per treatment.

3. Addition of compounds. This operation is carried out in a chemistry hood. Six microtiter plates have 245 microtiters of sterile water added to their wells ahead of time. 10 mg a.i. of the compounds are placed in 1 ml 1:1 acetone:methanol. 5 microliters of this solution is pipetted into the microtiter plates containing the sterile water according to the grid. There are 45 compounds and 3 scattered control treatments per plate. There are 2 replicates per treatment. 25 microtiters of solution is transferred to the inoculated plates with a 96 well replicator. The replicator is flame sterilized with alcohol, rinsed with sterile water, and blotted on sterile paper towels between each transfer.

TABLE 3

The Results of In-Vitro Plant Fungicide Tests

| Compound | Dose (PPM) | % Control | | | | | | | | |
|---|---|---|---|---|---|---|---|---|---|---|
| | | PYU | XAN | PIR | PHY | BOC | HEL | RHI | FUS | SEP |
| 1. | 25 | 100 | 0 | 100 | 100 | 100 | 100 | 100 | 100 | 100 |
| 2. | 25 | 95 | 0 | 75 | 95 | 0 | 75 | 100 | 100 | 95 |
| 3. | 25 | 100 | 0 | 75 | 75 | 0 | 90 | 95 | 100 | 95 |
| 4. | 25 | 100 | 0 | 95 | 95 | 0 | 100 | 90 | 100 | 100 |
| 5. | 25 | 100 | 0 | 100 | 100 | 50 | 95 | 100 | 100 | 100 |
| 6. | 25 | 100 | 0 | 100 | 100 | 100 | 100 | 100 | 100 | 100 |
| 7. | 25 | 100 | 0 | 100 | 100 | 100 | 100 | 100 | 100 | 100 |

TABLE 3-continued

The Results of In-Vitro Plant Fungicide Tests

| Compound | Dose (PPM) | % Control | | | | | | | | |
|---|---|---|---|---|---|---|---|---|---|---|
| | | PYU | XAN | PIR | PHY | BOC | HEL | RHI | FUS | SEP |
| 8. | 25 | 100 | 0 | 100 | 100 | 100 | 100 | 100 | 100 | 100 |
| 9. | 25 | 0 | 0 | 0 | 0 | 0 | 75 | 90 | 100 | 0 |
| 10. | 25 | 50 | 0 | 0 | 100 | 0 | 90 | 0 | 100 | 100 |
| 11. | 25 | 100 | 0 | 100 | 95 | 90 | 95 | 100 | 100 | 100 |
| 12. | 25 | 95 | 0 | 95 | 90 | 50 | 100 | 90 | 100 | 100 |
| 13. | 25 | 100 | 0 | 100 | 100 | 0 | 100 | 100 | 100 | 100 |
| 14. | 25 | 100 | 0 | 100 | 100 | 0 | 100 | 100 | 100 | 100 |
| 15. | 25 | 100 | 0 | 100 | 100 | 0 | 100 | 100 | 100 | 100 |
| 16. | 25 | 100 | 0 | 100 | 100 | 0 | 100 | 100 | 100 | 100 |
| 17. | 25 | 95 | 0 | 100 | 100 | 0 | 100 | 95 | 100 | 100 |
| 18. | 25 | — | 0 | 100 | 100 | 75 | 100 | 100 | 100 | 100 |
| 19. | 25 | 100 | 0 | 100 | 100 | 0 | 95 | 100 | 100 | 100 |
| 20. | 25 | 100 | 0 | 100 | 100 | 0 | 95 | 100 | 100 | 100 |
| 21. | 25 | 100 | 0 | 100 | 100 | 0 | 100 | 100 | 100 | 100 |
| 22. | 25 | 100 | 0 | 100 | 100 | 0 | 100 | 100 | 100 | 100 |
| 23. | 25 | 100 | 0 | 100 | 100 | 0 | 100 | 100 | 100 | 100 |
| 24. | 25 | 100 | 0 | 100 | 100 | 95 | 100 | 100 | 100 | 100 |
| 25. | 25 | 100 | 0 | 100 | 100 | 0 | 100 | 75 | 100 | 100 |
| 26. | 25 | 100 | 0 | 100 | 100 | 75 | 100 | 100 | 100 | 100 |
| 27. | 25 | 100 | 0 | 95 | 100 | 0 | 75 | 95 | 90 | 50 |
| 28. | 25 | 95 | 0 | 100 | 100 | 0 | 95 | 100 | 95 | 100 |
| 29. | 25 | 100 | 0 | 100 | 100 | 0 | 100 | 100 | 95 | 75 |
| 30. | 25 | 100 | 0 | 100 | 100 | 0 | 100 | 100 | 100 | 100 |
| 31. | 25 | 100 | 0 | 100 | 100 | 0 | 100 | 100 | 100 | 100 |
| 32. | 25 | 100 | 0 | 100 | 100 | 0 | 100 | 100 | 100 | 100 |
| 33. | 25 | 100 | 0 | 100 | 100 | 0 | 100 | 100 | 100 | 100 |
| 34. | 25 | 50 | 0 | 100 | 50 | 0 | 0 | 50 | 0 | 75 |
| 35. | 25 | 0 | 0 | 0 | 0 | 0 | 0 | 0 | 0 | 0 |
| 36. | 25 | 50 | 0 | 100 | 100 | 0 | 100 | 100 | 90 | 100 |
| 37. | 25 | — | — | — | — | — | — | — | — | — |
| 38. | 25 | 90 | 0 | 100 | 95 | 0 | 100 | 100 | 100 | — |
| 39 | 25 | 100 | 0 | 100 | 100 | 0 | 100 | 100 | 100 | 100 |
| 40 | 25 | 50 | 0 | 100 | 50 | 0 | 0 | 0 | 50 | 75 |
| 41 | 25 | 0 | 0 | 0 | 0 | 0 | 0 | 0 | 0 | |
| 42 | 25 | 50 | 0 | 100 | 100 | 0 | 100 | 100 | 90 | 100 |
| 43 | 25 | 90 | 0 | 100 | 95 | 0 | 100 | 100 | 100 | — |
| 44 | 25 | 90 | 0 | 100 | 95 | 0 | 100 | 100 | 100 | — |
| 45 | 25 | 0 | 0 | 90 | 0 | 0 | 0 | 0 | 50 | 0 |
| 46 | 25 | 0 | 0 | 100 | 0 | 0 | 50 | 50 | 100 | 0 |
| 47 | 25 | 100 | 0 | 100 | 100 | 100 | 100 | 100 | 100 | 100 |
| 48 | 25 | 100 | 0 | 100 | 100 | 100 | 100 | 100 | 100 | 100 |
| 49 | 25 | 100 | 0 | 100 | 100 | 100 | 100 | 100 | 100 | 100 |
| 50 | 25 | 100 | 0 | 95 | 100 | 100 | 95 | 95 | 95 | 95 |
| 51 | 25 | 100 | 0 | 100 | 100 | 100 | 100 | 100 | 100 | 100 |
| 52 | 25 | 100 | 0 | 100 | 100 | 100 | 100 | 100 | 100 | 100 |
| 53 | 25 | 100 | 0 | 100 | 100 | 100 | 100 | 100 | 100 | 100 |
| 54 | 25 | 100 | 0 | 100 | 100 | 100 | 100 | 100 | 100 | 100 |
| 55 | 25 | 100 | 0 | 100 | 100 | 100 | 100 | 100 | 100 | 100 |
| 56 | 25 | 100 | 0 | 100 | 100 | 100 | 100 | 100 | 100 | 100 |
| 57 | 25 | 100 | 0 | 100 | 100 | 100 | 100 | 100 | 100 | 100 |
| 58 | 25 | 100 | 0 | 100 | 100 | 90 | 100 | 100 | 100 | 100 |
| 59 | 25 | 100 | 0 | 100 | 100 | 100 | 100 | 100 | 100 | 100 |
| 60 | 25 | 0 | 0 | 100 | 0 | 0 | 50 | 0 | 0 | 0 |
| 61 | 25 | 100 | 0 | 100 | 100 | 100 | 100 | 100 | 100 | 100 |
| 62 | 25 | 0 | 0 | 0 | 0 | 0 | 0 | 0 | 0 | 0 |
| 63 | 25 | 100 | 0 | 100 | 100 | 100 | 100 | 100 | 100 | 100 |
| 64 | 25 | 100 | 0 | 100 | 100 | 100 | 100 | 100 | 100 | 100 |
| 65 | 25 | 100 | 0 | 100 | 100 | 100 | 100 | 100 | 100 | 100 |
| 66 | 25 | 100 | 0 | 95 | 100 | 100 | 100 | 100 | 100 | 10 |
| 67 | 25 | 100 | 0 | 100 | 100 | 100 | 100 | 100 | 100 | 100 |
| 68 | 25 | 100 | 0 | 100 | 100 | 90 | 100 | 100 | 100 | 100 |
| 69 | 25 | 100 | 0 | 100 | 95 | 50 | 95 | 50 | 0 | 95 |
| 70 | 25 | 100 | 0 | 100 | 100 | 75 | 100 | 100 | 100 | 100 |
| 71 | 25 | 100 | 0 | 100 | 100 | 90 | 100 | 100 | 100 | 100 |
| 72 | 25 | 100 | 0 | 100 | 100 | 0 | 50 | 75 | 0 | 95 |
| 73 | 25 | 0 | 0 | 0 | 50 | 0 | 50 | 0 | 0 | 0 |
| 74 | 25 | 100 | 0 | 100 | 100 | 0 | 75 | 100 | 0 | 0 |
| 75 | 25 | 90 | 0 | 75 | 90 | 0 | 0 | 100 | 0 | 0 |
| 76 | 12 | 0 | 0 | 100 | 100 | 0 | 0 | 50 | 0 | 50 |
| 77 | — | — | — | — | — | — | — | — | — | — |
| 78 | 25 | 100 | 0 | 100 | 100 | 0 | 75 | 100 | 100 | 100 |
| 79 | 25 | 100 | 0 | 100 | 100 | 75 | 100 | 100 | 100 | 50 |
| 80 | 25 | 100 | 0 | 100 | 100 | 50 | 100 | 100 | 100 | 50 |
| 81 | 25 | 100 | 0 | 100 | 100 | 0 | 100 | 100 | 0 | 0 |
| 82 | 25 | 100 | 0 | 100 | 100 | 100 | 100 | 100 | 100 | 100 |
| 83 | 25 | 100 | 0 | 100 | 100 | 0 | 75 | 100 | 100 | 50 |
| 84 | 25 | 100 | 0 | 100 | 100 | 50 | 100 | 100 | 100 | 100 |
| 85 | 25 | 100 | 0 | 100 | 100 | 50 | 100 | 100 | 100 | 100 |

TABLE 3-continued

The Results of In-Vitro Plant Fungicide Tests

| Compound | Dose (PPM) | PYU | XAN | PIR | PHY | BOC | HEL | RHI | FUS | SEP |
|---|---|---|---|---|---|---|---|---|---|---|
| 86 | 25 | 100 | 0 | 100 | 100 | 100 | 75 | 100 | 100 | 100 |
| 87 | — | — | — | — | — | — | — | — | — | — |
| 88 | — | — | — | — | — | — | — | — | — | — |
| 95 | 25 | 100 | 0 | 100 | 100 | 100 | 100 | 100 | 100 | 100 |
| 96 | 25 | 100 | 0 | 100 | 100 | 100 | 100 | 100 | 100 | 100 |
| 97 | — | — | — | — | — | — | — | — | — | — |
| 98 | 25 | — | — | — | 100 | — | — | 100 | 100 | — |
| 99 | 25 | — | — | — | 100 | — | — | 100 | 100 | — |
| 100 | 25 | 100 | 0 | 100 | 100 | 100 | 100 | 100 | 100 | 100 |
| 101 | 25 | 100 | 0 | 100 | 100 | 90 | 100 | 100 | 100 | 100 |
| 102 | 25 | 100 | 0 | 100 | 100 | 100 | 100 | 100 | 100 | 100 |
| 103 | 25 | 100 | 0 | 100 | 100 | 100 | 100 | 100 | 100 | 100 |
| 104 | 25 | 100 | 0 | — | 100 | 95 | 0 | 90 | 90 | 100 |
| 105 | 25 | 100 | 0 | — | 100 | 100 | 75 | 100 | 100 | 100 |
| 106 | 25 | 100 | 0 | 100 | 100 | 100 | 100 | 100 | 100 | 100 |
| 107 | 25 | 100 | 0 | 100 | 100 | 100 | 100 | 100 | 100 | 100 |
| 108 | 25 | 100 | 0 | 100 | 100 | 100 | 100 | 100 | 100 | 100 |
| 109 | 25 | 100 | 0 | 100 | 100 | 100 | 100 | 100 | 100 | 100 |
| 110 | 25 | 100 | 0 | 100 | 100 | 100 | 100 | 100 | 100 | 100 |
| 111 | 25 | 100 | 50 | 100 | 100 | 100 | 100 | 100 | 100 | 100 |
| 112 | 25 | 100 | 0 | 100 | 100 | 100 | 100 | 100 | 100 | 100 |
| 113 | 25 | 100 | 0 | 100 | 100 | 100 | 100 | 100 | 100 | 100 |
| 114 | 25 | 100 | 0 | 100 | 100 | 100 | 100 | 100 | 100 | 100 |

EXAMPLE 6

Agricultural Fungicide Evaluations of Compounds

The compounds of this invention were tested for fungicidal activity in vivo against cucumber downy mildew (CDM), rice blast (RB), rice sheath blight (RSB), tomato late blight (TLB), wheat powdery mildew (WPM), wheat stem rust (WSR) and wheat leaf rust (WLR) and the results are shown in Table 4. In tests on cereals (except for rice plants used for testing rice blast), the plants were trimmed about 24 hours prior to the application of the fungicide compound to provide a uniform plant height and to facilitate uniform application of the compound and inoculation with the fungus. The compounds were dissolved in a 2:1:1 mixture of water, acetone, and methanol, sprayed onto the plants, allowed to dry (four to six hours), and then the plants were inoculated with the fungus. Each test utilized control plants which were sprayed with the water, acetone, and methanol mixture and inoculated with the fungus. The remainder of the technique of each of the tests is given below and the results are reported as percent disease control (percentages of plants treated with the compounds of the present invention lacking disease signs or symptoms compared to the untreated control plants).

Cucumber Downy Mildew (CDM)

*Pseudoperonospora cubensis* was maintained on leaves of live Marketer cucumber plants in a constant temperature room at 65° F. to 75° F. in humid air with moderate light intensity for 7 to 8 days. A water suspension of the spores from infested leaves was obtained and the spore concentration was adjusted to about 100,000 per ml of water.

Marketer cucumber seedlings were inoculated by spraying the underside of the leaves with a DeVilbiss atomizer until small droplets were observed on the leaves. The inoculated plants were incubated in a mist chamber for 24 hours at about 70° F. and then subsequently incubated for 6 to 7 days in a controlled temperature room under mist at 65° F. to 75° F. Seven days after inoculation, the percent disease control was determined.

Rice Blast (RB)

Nato rice plants were inoculated with *Piricularia oryzae* (about 20,000 conidia per ml) by spraying the leaves and stems with an airbrush until a uniform film of inoculum was observed on the leaves. The inoculated plants were incubated in a humid environment (75° F. to 85° F.) for about 24 hours, then placed in a greenhouse environment (70° F. to 75° F.). Seven to eight days after inoculation, the percent disease control was determined.

Rice Sheath Blight (RSB)

*Pellicularia filamentosa* (f. sp. sasiki) was cultured on an autoclaved mixture of crushed rice seeds and potato dextrose broth (100 gms of rice seeds per 30 ml of potato dextrose broth) in a 500 ml Erlenmeyer flask. After 10 days, the culture was blended in a blender to produce a uniform inoculum. Approximately one teaspoon of inoculum was spread among Lebonnet rice seedlings on the soil surface of each pot (3 inch diameter). The inoculated seedlings were incubated for 5 days in a humidity cabinet (85° F. to 90° F.). Percent disease controls were determined immediately after removing the seedlings from the cabinet.

Tomato Late Blight (TLB)

*Phytophthora infestans* was cultured on four week old Pixie tomato plants in a controlled environment room (65° F. to 70° F. and 100% relative humidity). After storage, the spores were washed from the leaves with water and dispersed by DeVilbiss atomizer over three week old Pixie tomato plants which had been sprayed previously with experimental fungicides. The inoculated plants were placed in a humidity cabinet at 70° F. and constant mist for 24 hours for infection. The plants were then moved to the controlled environment room as above and scored after three more days incubation. Disease control levels were recorded as percent control four days after inoculation and five days after spraying the compounds.

Wheat Powdery Mildew (WPM)

*Erysiphe graminis* (f. sp. tritici) was cultured on Pennol wheat seedlings in a controlled temperature room at 65° F. to 75° F. Mildew spores were shaken from the culture plants onto Pennol wheat seedlings which had been sprayed previously with the fungicide compound. The inoculated seedlings were kept in a controlled temperature room at 65° F. to 75° F. and subirrigated. The percent disease control was rated 8 to 10 days after the inoculation.

Wheat Stem Rust (WSR)

*Puccinis graminis* (f. sp. Race 15B-2) was cultured on Wanzer wheat seedlings for a period of 14 days in a greenhouse. A water suspension of the spores from infested plants was obtained and the spore concentration was adjusted to about 200,000 spores per ml of deionized water. Wanzer wheat plants which had been previously treated with the fungicide compounds were inoculated by applying the stem rust spore suspension, until runoff, with a DeVilbiss atomizer at 5 lbs. per square inch air pressure. After inoculation, the plants were placed in a humid environment at approximately 75° F. where they were exposed to 12 hours of continuous darkness followed by a minimum of 3 to 4 hours of light having an intensity of about 500 footcandles. The temperature in the chamber did not exceed 85° F. At the end of the light period, the plants were placed in a greenhouse where they were permitted to grow for a period of two weeks at which time the percent disease control was determined.

Wheat Leaf Rust (WLR)

*Puccinis recondita* (f. sp. tritici Races PKB and PLD) was cultured on seven day old wheat (cultivar Fielder) over a 14 day period in the greenhouse. Spores were collected from the leaves with a cyclone vacuum or by settling on aluminum foil. The spores were cleaned by sieving through a 250 micron opening screen and stored or used fresh. Storage employed sealed bags in an Ultra-low freezer. When stored, spores must be heat shocked for two minutes at 40° F. before use. A spore suspension is prepared from dry uredia by adding 20 mg (9.5 million) per ml of Soltrol oil. The suspension is dispensed into gelatin capsules (0.7 ml capacity) which attach to the oil atomizers. One capsule is used per flat of twenty of the two inch square pots of seven day old Fielder wheat. After waiting for at least 15 minutes for the oil to evaporate from the wheat leaves, the plants are placed in a dark mist chamber (18°-20° C. and 100% relative humidity) for 24 hours. The plants are then put in the greenhouse for the latent period and scored after 10 days for disease levels. Protective and curative tests were inoculated one day after and two days, respectively, before spraying the plants with the test chemicals.

TABLE 4

Green House Test Results of Plant diseases Control

| Compound | Rate (ppm) | CDM | RB | SNW | TLB | WLR | WPM |
|---|---|---|---|---|---|---|---|
| 1. | 200 | 90 | 0 | 80 | 0 | 50 | 0 |
| 2. | 200 | 80 | 75 | 80 | 0 | 90 | 75 |
| 3. | 200 | 70 | 0 | 80 | 0 | 50 | 85 |
| 4. | 200 | 90 | 90 | 90 | 0 | 80 | 75 |
| 5. | 200 | 0 | 75 | 50 | 90 | 80 | 75 |
| 6. | 200 | 80 | 75 | 90 | 0 | 90 | 75 |
| 7. | 200 | 50 | 90 | 80 | 50 | 0 | 0 |
| 8. | 200 | 0 | 50 | 0 | 0 | 0 | 0 |
| 9. | 200 | 0 | 0 | 0 | 0 | 50 | 0 |
| 10. | 200 | 50 | 90 | 80 | 0 | 80 | 75 |
| 11. | 200 | 50 | 0 | 80 | 0 | 50 | 50 |
| 12. | 200 | 0 | 0 | 0 | 0 | 0 | 0 |
| 13. | 200 | 0 | 0 | 0 | 0 | 0 | 0 |
| 14. | — | — | — | — | — | — | — |
| 15. | 200 | 0 | 0 | 0 | 0 | 50 | 0 |
| 16. | 200 | 0 | 0 | 0 | 0 | 50 | 0 |
| 17. | 200 | 0 | 50 | 0 | 0 | 80 | 0 |
| 18. | 200 | — | 75 | 50 | 0 | 80 | 0 |
| 19. | 200 | 75 | 0 | 0 | 80 | 90 | 0 |
| 20. | 200 | 90 | 75 | 50 | 70 | 80 | 75 |
| 21. | 200 | 80 | 0 | 50 | 80 | 50 | 0 |
| 22. | 200 | 50 | 50 | 50 | 0 | 50 | 0 |
| 23. | 200 | 50 | 75 | 0 | 70 | 50 | 75 |
| 24. | 200 | 70 | 0 | 50 | 95 | 80 | 85 |
| 25. | 200 | 90 | 90 | 80 | 95 | 80 | 0 |
| 26. | 200 | 0 | 0 | 0 | 95 | 0 | 50 |
| 27. | 200 | 80 | 0 | 0 | 85 | 80 | 0 |
| 28. | 200 | 70 | 75 | 0 | 80 | 80 | 0 |
| 29. | 200 | 90 | 0 | 50 | 80 | 80 | 90 |
| 30. | 200 | 95 | 0 | 0 | 80 | 80 | 75 |
| 31. | 200 | 50 | 90 | 50 | 85 | 80 | 75 |
| 32. | 200 | 0 | 0 | 50 | 90 | 80 | 0 |
| 33. | 200 | 0 | 0 | 0 | 70 | 50 | 85 |
| 34. | 200 | 90 | 99 | 80 | 80 | 80 | 85 |
| 35. | 200 | 70 | — | 0 | 0 | 50 | 0 |
| 36. | 200 | 70 | — | 50 | 85 | 95 | 0 |
| 37. | 200 | 0 | 50 | 0 | 0 | 25 | 75 |
| 38. | 200 | 70 | 0 | 0 | 0 | 0 | 0 |
| 39. | 200 | 0 | 0 | 50 | 90 | 80 | 0 |
| 40. | 200 | 50 | 0 | 0 | 80 | 50 | 90 |
| 41. | 200 | 0 | 0 | 0 | 70 | 50 | 85 |
| 42. | 200 | 0 | — | 0 | 85 | 50 | 0 |
| 43. | 200 | 70 | — | — | 0 | 50 | 0 |
| 44. | 200 | 70 | — | 50 | 85 | 95 | 0 |
| 45. | 200 | 0 | 50 | 0 | 0 | 25 | 75 |
| 46. | 200 | 70 | 0 | 0 | 0 | 0 | 0 |
| 47. | 200 | 0 | — | 50 | — | 80 | 0 |
| 48. | 200 | 50 | — | 50 | — | 50 | 90 |
| 49. | 200 | 0 | — | 80 | 85 | 50 | 0 |
| 50. | 200 | 0 | — | 0 | 0 | 50 | 0 |
| 51. | 200 | 0 | — | 0 | 90 | 50 | 0 |
| 52. | 200 | 0 | — | 0 | 0 | 80 | 0 |
| 53. | 200 | 0 | — | 0 | 0 | 80 | 0 |
| 54. | 200 | 0 | — | 80 | 0 | 80 | 85 |
| 55. | 200 | 70 | — | 50 | 0 | 80 | 0 |
| 56. | 200 | 0 | — | 50 | 0 | 80 | 50 |
| 57. | 200 | 70 | — | 80 | 85 | 80 | 100 |
| 58. | 200 | 95 | — | 0 | 70 | 90 | 90 |
| 59. | 200 | 90 | 0 | 50 | 0 | 50 | 0 |
| 60. | 200 | 85 | — | 0 | 0 | 0 | 0 |
| 61. | 200 | 0 | — | — | 50 | 0 | 0 |
| 62. | — | — | — | — | — | — | — |
| 63. | 200 | 90 | — | — | 50 | 90 | 0 |
| 64. | — | — | — | — | — | — | — |
| 65. | 200 | 90 | — | — | 90 | 90 | 0 |
| 66. | 200 | 75 | — | — | 0 | 99 | 0 |
| 67. | 200 | 85 | — | — | 95 | 90 | 0 |
| 68. | 200 | 50 | — | — | 50 | 99 | 0 |
| 69. | — | — | — | — | — | — | — |
| 70. | 200 | 80 | — | — | 0 | 0 | 0 |
| 71. | — | — | — | — | — | — | — |
| 72. | — | — | — | — | — | — | — |
| 73. | 200 | 90 | — | — | 0 | 85 | 85 |
| 74. | 200 | 0 | — | — | 50 | 75 | 0 |
| 75. | 200 | 0 | — | — | 0 | 95 | 0 |
| 76. | 200 | 90 | — | — | 0 | 95 | 0 |
| 77. | — | — | — | — | — | — | — |
| 78. | — | — | — | — | — | — | — |
| 79. | 200 | 75 | — | — | 75 | 85 | 0 |
| 80. | 200 | 50 | — | — | 75 | 75 | 0 |
| 81. | 200 | 0 | — | — | 0 | 75 | 0 |
| 82. | 200 | 50 | — | — | 0 | 0 | 0 |
| 83. | 200 | 85 | — | — | 75 | 95 | 0 |
| 84. | — | — | — | — | — | — | — |
| 85. | — | — | — | — | — | — | — |

TABLE 4-continued

Green House Test Results of Plant diseases Control

| Compound | Rate (ppm) | CDM | RB | SNW | TLB | WLR | WPM |
|---|---|---|---|---|---|---|---|
| 86 | 200 | 75 | — | — | 85 | 75 | 0 |
| 87 | — | — | — | — | — | — | — |
| 88 | 200 | 90 | — | — | 0 | 0 | 0 |
| 89 | — | — | — | — | — | — | — |
| 90 | — | — | — | — | — | — | — |
| 91 | — | — | — | — | — | — | — |
| 92 | 200 | 70 | — | — | — | 95 | 0 |
| 93 | 200 | 95 | — | — | 0 | 75 | 0 |
| 94 | 200 | 100 | — | — | 0 | 90 | 0 |
| 95 | — | — | — | — | — | — | — |
| 96 | 200 | 90 | — | — | 0 | 99 | 0 |
| 97 | — | — | — | — | — | — | — |
| 98 | 200 | 90 | — | — | 90 | 95 | 0 |
| 99 | — | — | — | — | — | — | — |
| 100 | — | — | — | — | — | — | — |
| 101 | 200 | 0 | — | — | 0 | 0 | 0 |
| 102 | 200 | 0 | — | — | 0 | 75 | 0 |
| 103 | 200 | 0 | — | — | 0 | 50 | 0 |
| 104 | — | — | — | — | — | — | — |
| 105 | — | — | — | — | — | — | — |
| 106 | — | — | — | — | — | — | — |
| 107 | — | — | — | — | — | — | — |
| 108 | — | — | — | — | — | — | — |
| 109 | — | — | — | — | — | — | — |
| 110 | 200 | — | — | 50 | 75 | 80 | 0 |
| 111 | — | — | — | — | — | — | — |
| 112 | — | — | — | — | — | — | — |
| 113 | — | — | — | — | — | — | — |
| 114 | 200 | — | — | 50 | 75 | 90 | 0 |
| 115 | — | — | — | — | — | — | — |
| 116 | 200 | 100 | — | — | 75 | 90 | 0 |

TABLE 5

Antialgal Test Results Against Green Alga

| Compound # | MIC (ppm) Chlorella |
|---|---|
| 85 | 0.25 |
| 87 | 4 |
| 88 | <0.12 |
| 89 | <0.12 |
| 90 | <0.12 |
| 107 | <0.12 |
| 108 | 8 |
| 109 | 8 |
| 110 | 4 |
| 111 | >250 |
| 112 | 0.25 |
| 113 | 8 |
| 114 | 8 |
| 120 | 125 |
| 121 | <0.12 |

What is claimed is:

1. A compound of the formula

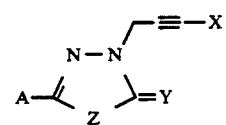

wherein A is selected from the group consisting of hydrogen, ($C_1$–$C_{18}$) straight or branched alkyl; ($C_3$ to $C_8$) cycloalkyl; ($C_3$ to $C_6$) alkenyl; ($C_3$ to $C_5$) alkynyl; ($C_7$ to $C_{12}$) aralkyl; ($C_6$ to $C_{12}$) aryl; ($C_6$ to $C_{12}$) aryl substituted with 1 to 3 substituents selected from the group consisting of halogen, ($C_1$ to $C_4$) alkyl ($C_1$ to $C_4$) alkoxy, nitro, cyano, carboxyl ($C_1$ to $C_4$) alkoxycarbonyl, ($C_1$ to $C_4$) alkyl thio, -S(O)n$R^2$ where n is 1 or 2 and $R^2$ is ($C_1$–$C_4$) alkyl; and a halo-substituted, nitro-substituted, or un-substituted moiety selected from the group consisting of 2-thienyl, 3-thienyl, 2-furyl, 3-furyl, 2-pyridyl, 3-pyridyl, and 4-pyridyl;

Y is selected from the group consisting of O, S, and N-R;

Z is S;

R is selected from the group consisting of hydrogen, substituted or unsubstituted alkyl, substituted or unsubstituted alkenyl, substituted or unsubstituted alkynyl, substituted or unsubstituted phenyl, and substituted or unsubstituted heterocyclic; and X is selected from the group consisting of I and Br.

2. Compound according to claim 1 wherein A is selected from the group consisting of hydrogen, 4-chlorophenyl, 3-chlorophenyl, 2-methylphenyl, 4-methylphenyl, 3-methylphenyl, 2-thienyl, 2-nitrophenyl, 3-nitrophenyl, 4-trifluoromethylphenyl, 2-methoxyphenyl, 4-methoxyphenyl, 3-methoxyphenyl, 4-bromophenyl, 2-fluorophenyl, 2-chloro-4-nitrophenyl, 2,4-dichlorophenyl, 3,4-dichlorophenyl, 2,4,5-trichlorophenyl methyl, t-butyl, phenyl, 4-nitrophenyl, 3-fluorophenyl, 1-naphthyl, 2-naphthyl, 3-pyridyl, 3-bromophenyl, 3-ethoxyphenyl, n-propyl, 2-chlorophenyl, cyclohexyl, 2-furyl, 3,5-dimethoxyphenyl, 2,5-dimethoxyphenyl, 3,4,5-trimethoxyphenyl, 2,5-dichlorophen and methyl n-butyl.

3. Compound according to claim 1 wherein X is I.

4. Compound according to claim 3 wherein Y is O.

5. Process comprising applying or incorporating a sufficient amount of a compound of claim 1 to control the growth of fungi into or onto a locus subject to attack by fungi.

6. Process comprising applying or incorporating a sufficient amount of a compound of claim 1 to control the growth of bacteria into or onto a locus subject to attack by bacteria.

* * * * *